(12) United States Patent
Lünnemann et al.

(10) Patent No.: US 11,001,402 B2
(45) Date of Patent: May 11, 2021

(54) CELL TRAVERSE WITH INSERT ELEMENTS FOR A FILLING MACHINE

(71) Applicants: Bernd Lünnemann, Düsseldorf (DE); Klaus Naber, Kempen (DE); Thomas Cramer, Syke (DE)

(72) Inventors: Bernd Lünnemann, Düsseldorf (DE); Klaus Naber, Kempen (DE); Thomas Cramer, Syke (DE)

(73) Assignee: SIG Technology AG, Neuhausen am Rheinfall (CH)

( * ) Notice: Subject to any disclaimer, the term of this patent is extended or adjusted under 35 U.S.C. 154(b) by 0 days.

(21) Appl. No.: 16/732,922

(22) Filed: Jan. 2, 2020

(65) Prior Publication Data

US 2020/0140131 A1    May 7, 2020

Related U.S. Application Data

(63) Continuation of application No. PCT/EP2018/067653, filed on Jun. 29, 2018.

(30) Foreign Application Priority Data

Jul. 3, 2017 (DE) ..................... 10 2017 114 760.8

(51) Int. Cl.
*B65B 43/54* (2006.01)
*B65B 43/00* (2006.01)
(Continued)

(52) U.S. Cl.
CPC ............... *B65B 43/52* (2013.01); *B65B 3/04* (2013.01); *B65B 43/54* (2013.01); *B65B 55/025* (2013.01); *B65G 65/32* (2013.01); *B65G 2207/30* (2013.01)

(58) Field of Classification Search
None
See application file for complete search history.

(56) References Cited

U.S. PATENT DOCUMENTS 4,566,251 A     1/1986 Spisak et al.
7,395,842 B2 *  7/2008 Dyer ...................... B65B 3/045
                                                        141/10
(Continued)

FOREIGN PATENT DOCUMENTS

DE    3701079 A1    7/1988
DE    20320380 U1   6/2004
(Continued)

*Primary Examiner* — Kavel Singh
(74) *Attorney, Agent, or Firm* — Reinhart Boerner Van Deuren P.C.

(57) ABSTRACT

Embodiments of a cell traverse for an aseptic region of a filling machine for filling packages with flowable products are provided. The cell traverse includes a frame structure with a first lateral longitudinal structure and a second lateral longitudinal structure opposite the first longitudinal structure. Also included are a plurality of transverse elements arranged between the first and second longitudinal structures and connecting the longitudinal structures. Between the longitudinal structures and the transverse elements a plurality of cells of the cell traverse are formed for receiving packages to be filled. The cell traverse also includes insert elements, which each have the frame structure, in particular at least one longitudinal structure and/or at least one transverse element, and at least some of the insert elements are detachably connected to the frame structure of the cell traverse.

15 Claims, 8 Drawing Sheets

(51) Int. Cl.
*B65B 3/04* (2006.01)
*B65G 65/32* (2006.01)
*B65B 43/52* (2006.01)
*B65B 55/02* (2006.01)

(56) References Cited

U.S. PATENT DOCUMENTS

| | | | |
|---|---|---|---|
| 8,079,460 B2 * | 12/2011 | Kurz | B65B 59/003 |
| | | | 198/473.1 |
| 9,440,754 B2 * | 9/2016 | Colangelo | B65B 3/022 |
| 2010/0263324 A1 | 10/2010 | Jendrichowski et al. | |

FOREIGN PATENT DOCUMENTS

| | | |
|---|---|---|
| DE | 10 2012 102 812 A1 | 10/2013 |
| DE | 10 2012 112 792 A1 | 6/2014 |
| DE | 10 2015 101 751 A1 | 8/2016 |
| DE | 10 2015 114 457 A1 | 3/2017 |
| DE | 10 2015 122 529 A1 | 6/2017 |
| GB | 853 696 A | 11/1960 |
| JP | Hei 4-125228 U | 11/1992 |
| JP | Hei 11-165712 A | 6/1999 |
| JP | 2002-037218 A | 2/2002 |
| JP | 2006-206086 A | 8/2006 |

\* cited by examiner

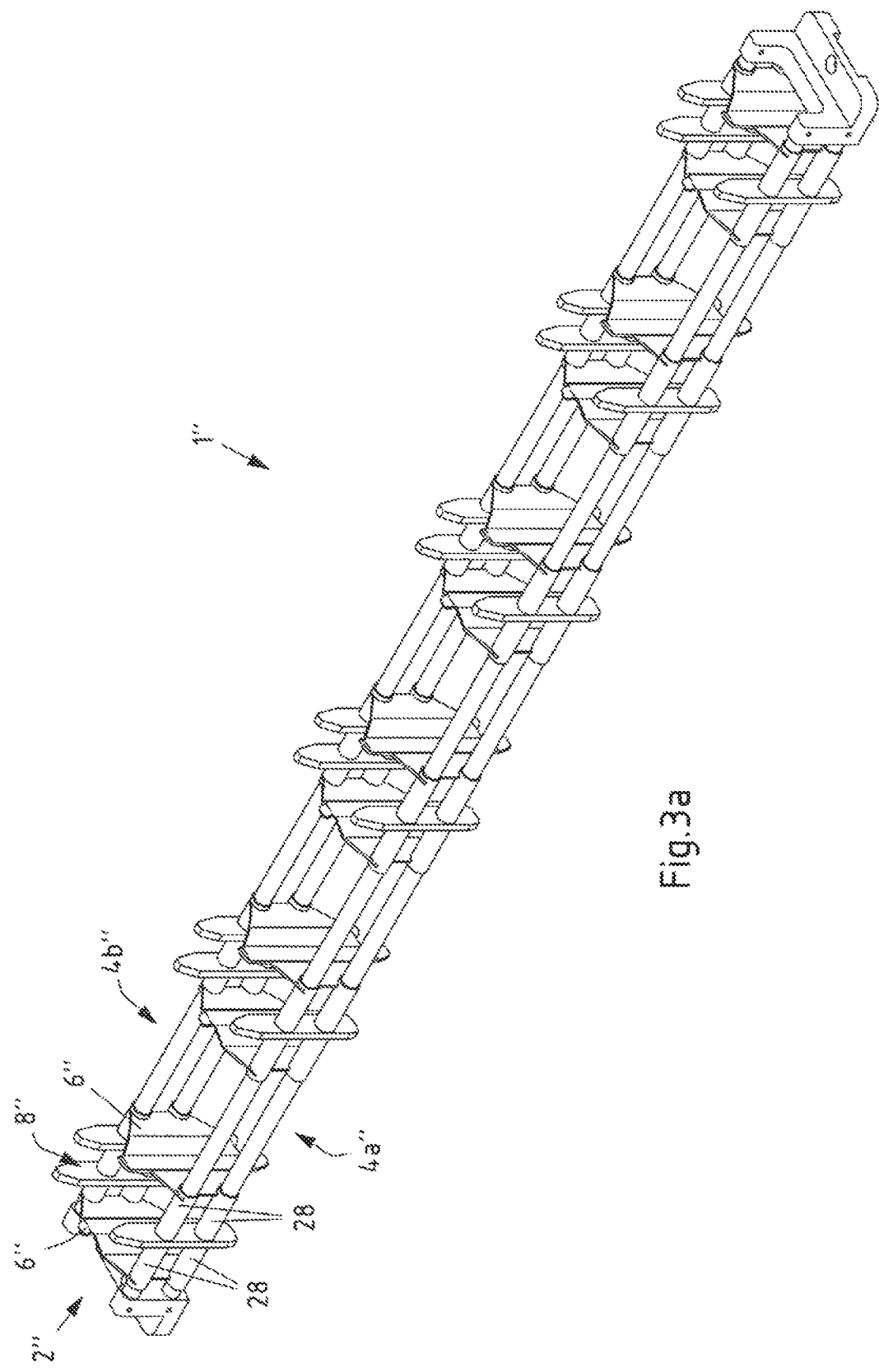

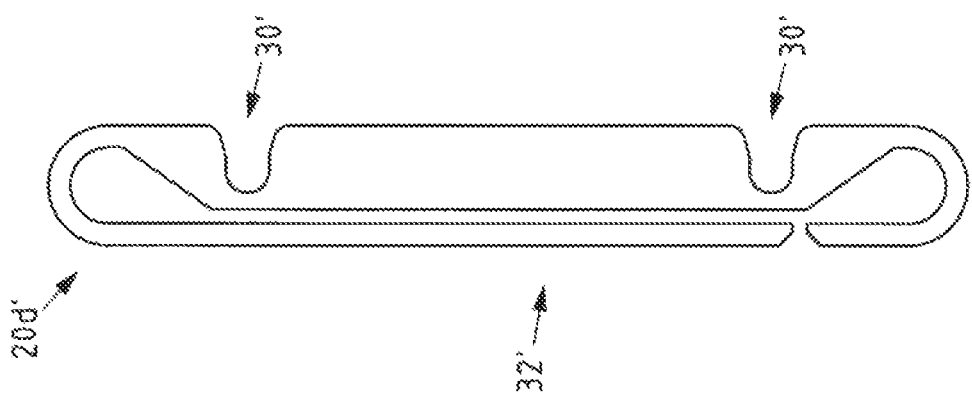
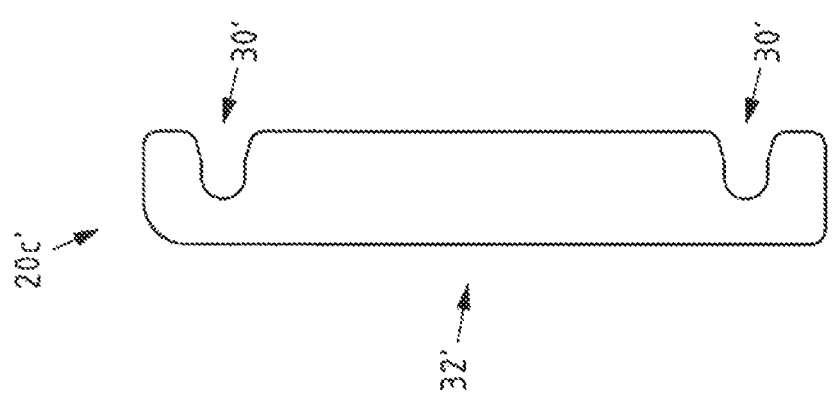
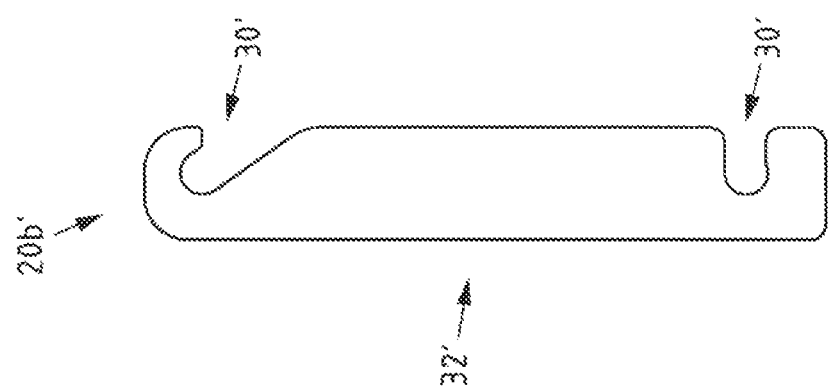

CELL TRAVERSE WITH INSERT ELEMENTS FOR A FILLING MACHINE

CROSS-REFERENCE TO RELATED PATENT APPLICATIONS

This patent application is a continuation of PCT/EP2018/067653, filed Jun. 29, 2018, which claims priority to German Application No. 10 2017 114 760.8, filed Jul. 3, 2017, the entire teachings and disclosure of which are incorporated herein by reference thereto.

FIELD

The invention concerns a cell traverse for an aseptic area of a filling machine for filling packages with flowable products. The invention also concerns the use of a cell traverse according to the invention and a filling machine.

BACKGROUND

Generic filling machines are used to fill packages preferably with flowable foods. In particular, packages which are open on one side to provide an opening for filling the packages are used as packages. The packages may, for example, be carton composite packages formed from a packaging material in the form of a laminate comprising a cardboard layer and outer, in particular thermoplastic, plastic layers such as polyethylene (PE). The carton gives the packages sufficient stability so that they can be easily handled and stacked, for example. The plastic layers protect the carton from moisture and allow the packaging material to be sealed to form a tight package. In addition, further layers, such as an aluminium layer, may be provided to prevent diffusion of oxygen and other gases through the package. However, a package can also be a bottle, such as a PET bottle.

Packages are typically filled with food under sterile conditions. Not only the food to be filled, but also the package has to be sterilized. For this purpose, the food is normally heated for a certain period of time. The packages are usually first blown out with sterile hot air. A sterilizing agent which is typically or at least contains hydrogen peroxide is then introduced into the packages heated in this way. Since the package is preheated, high reaction rates are achieved during sterilisation and condensation is prevented from forming in the package. Moisture and residual hydrogen peroxide are then removed from the package by drying the package with drying air, which is preferably hot and sterile. Then, under sterile conditions, the sterile package is filled with the product, which is also sterile and predominantly flowable, especially liquid. Such products are typically foods such as juices, milk, sauces and the like. In addition to at least one liquid component, foodstuffs may also contain chunky components. After the packages have been filled, they are sealed in a sterile atmosphere.

During sterilisation and/or filling, the packages can be transported continuously through the filling machine at a constant speed as required. Alternatively, however, the packages are moved through the filling machine in cycles, i.e. step by step. The packages can take up specific positions one after the other for a certain period of time, in which the packages can be pressurised with hot air, sterilising agent and/or drying air or filled with the product to be filled, standing still via at least one nozzle.

The targeted transport of the packages through the filling machine is often facilitated by a transport device which has a series of revolving movable cell traverses with cells. The cells of a cell traverse typically pass through the same process step of the filling machine at the same time. By providing several parallel cell traverses one behind the other, cells arranged one behind the other are created. In a feeding area, the packages are transferred one after the other from a feeding device into the cells of the cell traverses arranged one behind the other. The packages are then moved in the cells through a filling area to a dispensing area, during which the packages are sterilized, filled and sealed as described. An aseptic or sterile area (aseptic area) is required from sterilisation to sealing of the package and especially when filling the packages. The cell traverses must therefore not introduce any germs or other impurities into the aseptic area. At the same time, the cell traverses must be able to withstand aseptic conditions (high temperatures, water, sterilising agents such as hydrogen peroxide). In the delivery area, the packages are then delivered via a corresponding delivery device. The now empty cells are then moved back to the feed area via a return area in order to be able to pick up the packages, in particular packages open on one side, to be filled again. Typically, the filling area and the return area are approximately linear, while between them there are deflection areas in which the transport direction of the cells is reversed. For reasons of space, the feed and discharge devices are typically assigned to the deflection areas.

The cell traverses are designed in such a way that they are also suitable for accommodating slightly different package sizes with the same cross section. That means, that the cell is preferably suitable for accommodating packages of the same cross-section but of different heights. In practice, groups from 80 ml to 250 ml or 500 ml to 1000 ml or 1400 ml to 2000 ml or similar ranges occur. However, if geometrically different packages (e.g. different groups) are to be filled with the filling machine, it is often necessary to replace the cell traverses. Since the transport equipment of a filling machine often comprises dozens of cell traverses and a change is correspondingly time-consuming, this can lead to a not inconsiderable production standstill. In addition, different groups of cell traverses must be kept available. Apart from the cell geometry, other properties of the cell traverses, such as material properties or flow properties of the cell traverses, can also lead to these having to be exchanged.

At the same time, it must be taken into account that the cell traverses must always meet further requirements, in particular with regard to their resistance if they are exposed to the conditions prevailing in the aseptic area of the filling machine (heat, water, sterilising agents) or hygienic requirements.

BRIEF SUMMARY

Therefore, the present invention is based on the task of designing and arranging cell traverses in such a way that they can be used economically and at the same time meet the requirements resulting from their use in a filling machine, in particular with regard to durability and hygiene.

According to a first teaching of the present invention, the problem is solved with a cell traverse, which has a frame structure with at least one first lateral longitudinal structure, with at least one second lateral longitudinal structure opposite the first longitudinal structure, and with several transverse elements arranged between the first and second longitudinal structures and connecting the longitudinal structures, wherein a plurality of cells lying next to one another in the longitudinal direction of the cell traverse are formed between the longitudinal structures and the transverse elements for receiving packages filled or to be filled, wherein the cell traverse further comprises insert elements which are each connected or connectable to the frame structure, in particular at least one longitudinal structure and/or at least one, preferably two transverse elements, and wherein at least a part of the insert elements is detachably connected or connectable to the frame structure of the cell traverse.

According to a second teaching, the task is also solved by using a cell traverse according to the invention for a filling machine for filling packages with flowable products.

According to a third teaching, the task is also solved by a filling machine for filling packages with flowable products with an endlessly circulating transport device for transporting the packages through the filling machine, whereby the transport device comprises several cell traverses according to the invention.

While the state of the art primarily pursues an integral construction of the cell traverses or at least an undetachable and, in particular, form-fit connection of individual parts of the cell traverses, the present invention pursues a different approach.

As the cell traverse, in addition to the frame structure, also comprises insert elements which are detachably connected or connectable to the frame structure, the geometry and properties of the cell traverse and in particular of the cells can be adapted individually and independently of the frame structure. The insert elements can therefore be regarded as interchangeable elements. In particular, it was shown that, contrary to expectations, the detachable connection between the insert elements and the frame structure has no or no relevant negative effects on the properties of the cell traverse, such as resistance and hygiene. By replacing only the insert elements instead of the entire cell traverse, the cost-effectiveness of the filling machine can also be increased, since, for example, the same cell traverses or frame structures with different insert elements can be used for a wider range of packages.

For reasons of stability and rapid interchangeability, it has proved to be particularly advantageous if the insert elements each have (at least and preferably exactly) two connection areas for connection to the frame structure. For example, a respective insert element has two connecting areas for connection with a longitudinal structure. For example, a respective insert element has two connecting areas for connection with two transverse elements.

The fact that the cell traverse is intended for an aseptic area means that it is suitable or designed for traversing an aseptic area and that it is durable, especially for years, even under environmental conditions which prevail in the aseptic area, for example due to water, hot air and/or sterilising agents.

The longitudinal elements and/or the transverse elements are preferably made of a metal, preferably steel, which enables a stable frame structure with high resistance and a secure connection between frame structure and insert elements. For hygienic reasons, it is particularly preferred if the above elements are made of stainless steel, preferably a stainless steel with the material number 1.4301 (in particular 17.5-19.5% Cr and 0-0.1% N) or a higher quality stainless steel in this group. Preferably the steel used has a PREN index (Pitting Resistance Equivalent Number) greater than 15, preferably greater than 17. For example, a stainless steel of grade 1.4301 has a PREN index of 17.5-21.1. The PREN index can be calculated in particular according to the formula PREN=1×% Cr+3.3×% Mo+16×% N (w/w) or alternatively according to the formula PREN=1×% Cr+3.3×(% Mo+0.5×% W)+16×% N.

The first and second longitudinal structures preferably form a longitudinal side of the frame structure of the cell traverse. The first and second longitudinal sides are preferably parallel. The transverse elements are preferably perpendicular to the longitudinal elements.

The several cells lying next to each other in the longitudinal direction of the cell traverse do not have to lie directly next to each other. Rather, it is preferred if the cells are formed lying next to each other at a distance in the longitudinal direction. The fact that the cells are designed to hold packages filled or to be filled means that a cell can hold all or part of the pack, for example. An upper part of the package taken up in a cell preferentially protrudes beyond the formed cell.

The (empty) packages are preferably picked up or inserted in a transverse (especially vertical) direction of insertion into the cells in relation to the longitudinal direction of the cell traverse and in relation to the transport direction of the cell traverse.

By the fact that the transport device of the filling machine according to the invention comprises several cell traverses according to the invention, it has a plurality of cells for receiving the packages. In particular, the endlessly circulating transport device has a feed region which is assigned a feed device for feeding packages to be filled. In addition, the transport device preferably has a delivery area to which a delivery device for delivering the packages is assigned. The aseptic area with filling area in particular is then provided between the feed area and the discharge area. A return area is preferably provided between the discharge area and the feed area.

In accordance with a preferred embodiment of the cell traverse according to the invention, at least some of the insert elements provide a contact area for filled or to be filled packages which are to be accommodated or received in the cells. In this way, the insert elements allow the geometry and/or properties (e.g. thermal properties) of the areas of the cell traverse to be brought into contact with the packages and/or the geometry of the receiving area provided by the cell (e.g. for different package sizes) to be adapted individually and independently of the frame structure. This means that different sets of cell traverses no longer have to be maintained for different package sizes and/or geometries. The insert elements can also have a guiding function in order to achieve a process-reliable introduction of the packages into the cells. The insert elements can therefore be regarded as package guides.

For example, the contact area between the package and the cell traverse is provided exclusively by the insert elements. Therefore, there is preferably no further contact between package and frame structure.

The insert elements, for example, are elongated. When used, these preferably run transversely (especially perpendicularly) to the longitudinal direction of the frame structure (i.e. especially in the insertion direction).

In accordance with a preferred embodiment of the cell traverse according to the invention, the insert elements for providing the contact area have at least one resilient section. This ensures a secure fit of packages in the cells without damaging the packages. A resilient section is particularly possible with an insert made of plastic due to the elasticity of plastic. For example, the insert element for the production of the resilient section is locally thinned and/or has a free-swinging arm on one side.

In accordance with a preferred embodiment of the cell traverse according to the invention, at least some of the insert elements are flow guiding structures, which can be arranged or are arranged between two adjacent cells. The flow guiding structures serve to direct gas flows within the aseptic area of the filling machine. Preferably, the aseptic area is permanently purged with a gas (e.g. sterile air), so that a downward gas flow is provided in the aseptic area in order to tend to lead any impurities downwards. In addition, the slight overpressure in the aseptic area achieved in this way effectively prevents the possible introduction of germs by ambient air. In particular, the flow guiding structures are designed in such a way that they increase the flow resistance in the area between adjacent cells. This results in a higher gas flow in the area of the cells where the packages are filled and contamination is to be avoided. For example, the flow guiding structures form a funnel running in the direction of insertion. For example, a flow guide structure comprises one or more baffles. Due to the flow guiding structures provided as detachable insert elements, the cell traverses can be used both with and without flow guiding structures or the flow guiding structures can be quickly exchanged.

In accordance with a preferred embodiment of the cell traverse in accordance with the invention, at least some of the insert elements are connected or connectable to the frame structure of the cell traverse by means of a clip connection, a screw connection and/or, in particular, a lockable plug-in connection. It has been shown that such compounds are sufficiently resistant to the ambient conditions prevailing in the filling machine and do not adversely affect the deposition of contamination.

The insert elements are preferably connected or connectable to the frame structure of the cell traverse without further aids (such as a clip connection). A clip connection is understood in particular as a latching connection between the insert element and the frame structure of the cell traverse, which is produced by overcoming a certain assembly force. In the case of a clip connection, an insert element which can be connected thereto has, for example, at least one, preferably at least two locking grooves, in particular for connection to respective transverse elements. For this purpose, a transverse element can, for example, have a circumferential groove at the corresponding point, so that the transverse element only has to have the diameter suitable for connection with the snap-in groove of the insert element in the area of the groove.

In accordance with a preferred embodiment of the cell traverse according to the invention, at least some of the insert elements can be connected and/or detached from the cell traverse without tools. This means that, in particular, the required assembly force can be applied in this case without the need for additional tools. This can be particularly advantageous with a clip connection.

For example, a part of the insert elements is connected or connectable by means of a clip connection (in particular with the transverse elements) and a part of the insert elements by means of a screw connection (in particular with the longitudinal structure).

In accordance with a preferred embodiment of the cell traverse according to the invention, at least part of the insert elements is made of or includes a plastic, in particular a plastic based on polyethylene terephthalate (PET-P) or polyether ether ketone (PEEK). Examples of polyethylene terephthalate-based plastics include Ertalyte PET-P and Ertalyte TX from Quadrant. In the case of insert elements that provide a contact area for the packages, the frame structure can then be made of metal, for example, while the lower thermal conductivity of the plastic nevertheless results in a lower heat transfer from the packages to the cell traverse. This avoids excessive heat transfer from the heated package to the frame structure, which in turn reduces or avoids cooling and associated condensation (e.g. of the sterilizing agent) in the package. This in turn reduces the risk of contamination of the packages by foreign substances.

For example, the plastic contains a homogeneously distributed solid lubricant, which enables very high wear resistance and a lower coefficient of sliding friction.

The plastics mentioned have advantageous properties, in particular with regard to the manufacturing tolerances required for the cell traverses.

The use of so-called plastic screws (made of stainless steel) is particularly advantageous in the case of a screw connection in conjunction with plastic insert elements, as the plastic can swell and seal existing gaps.

According to a preferred embodiment of the cell traverse according to the invention, at least a part of the insert elements is made of a metal. Insert elements made of metal, in particular steel, allow a particularly low risk of breakage during replacement or operation.

In order to reduce both the risk of condensation and at the same time achieve a low risk of breakage of the insert elements, at least some of the insert elements have a metal reinforcement in accordance with a preferred embodiment of the cell traverse according to the invention. For example, internal metal inserts are provided in the insert elements made of plastic.

According to a preferred embodiment of the cell traverse according to the invention, the roughness (especially the average roughness Ra in μm) of the insert elements (especially if they are made of plastic), especially in the contact area provided, is at most 1.6, preferably at most 1.2. This allows not only trouble-free insertion and removal of the packages into the cells, but at the same time a high cleanability.

According to a preferred embodiment of the cell traverse according to the invention, the contact area provided by insert elements for filled or to be filled packages which are to be accommodated or received in the cells is not more than 35%, preferably not more than 30%, particularly preferably not more than 25% of the package outer area. This prevents as far as possible unwanted heat transfer from the package to the cell traverse and thus unwanted condensation. The indicated values are preferred for insert elements made of plastic or plastic. If the insert elements are made of metal, it is further preferred if the contact area provided by insert elements for filled or to be filled packages which are to be accommodated or received in the packages is not more than 10%, preferably not more than 7%, particularly preferably not more than 5% of the package outer area.

In accordance with the preferred embodiment of the cell traverse according to the invention, at least some of the transverse elements are connected to the longitudinal structures exclusively in a form-fit and/or force-fit manner. It has been shown that an economical production of the cell traverse is possible by an exclusively form-fit and/or force-fit connection and in particular connections of the transverse elements with the longitudinal structures can be achieved reliably with low distortion and with particularly small gap sizes in the connection area (in particular less than 0.02 mm). Surprisingly, such compounds are also resistant to the conditions prevailing in the aseptic area of a filling machine and meet the requirements. Preferably, therefore, all transverse elements of the frame structure of the cell traverse are connected to the longitudinal structures exclusively in a form-fit and/or force-fit manner.

According to a preferred embodiment of the cell traverse according to the invention, at least a part of the transverse elements is connected to the longitudinal structures by means of a rivet connection. It has been shown that an economical production of the cell traverse with low warpage and low gap formation can be achieved particularly by a riveted joint and that the accumulation of impurities and the risk of contamination of the filled product by microorganisms can be reduced as a result. For example, a rivet is used for each joint between cross member and longitudinal member. A rivet preferably lies coaxial to the respective transverse element. Riveted joints can be made, for example, using solid rivets, blind rivets or self-pierce rivets. The riveted joint can be form-fit and optionally force-fit. For example, cold riveting can be used to produce an exclusively form-fit connection, while hot riveting can be used to create an additional frictional connection by shrinking as the rivet cools.

According to a preferred embodiment of the cell traverse according to the invention, at least a part of the transverse elements is connected to the longitudinal structures by means of a screw connection. It has been shown that, alternatively, an economical production of the cell traverse with low warpage and low gap formation can be achieved by means of a screw connection and that as a result the accumulation of impurities and the risk of contamination of the filled product by microorganisms can be reduced.

According to a preferred embodiment of the cell traverse according to the invention, at least a part of the transverse elements is connected to the longitudinal structures by means of a plug-in connection. The plug connection, for example, is an exclusively form-fit connection. For example, a plug-in connection is achieved by engaging the transverse elements in slots in the longitudinal structure and/or by sliding sleeves onto the longitudinal structure. For example, the connection can be made by threading the transverse elements and the sleeves onto the longitudinal structure so that the transverse elements can be form-fit connected to the longitudinal structure at defined positions. For example, the sleeves and/or longitudinal struts of the longitudinal structure have at least some circumferential grooves or slots in which the transverse elements can engage. The transverse elements together with the sleeves can then first be pushed or pushed onto the longitudinal struts of the longitudinal structure. A fixed connection (locking) between transverse elements and longitudinal structure then results, for example, from a fixed connection at the end between the first lateral longitudinal structure and the second lateral longitudinal structure. Alternatively or additionally, the longitudinal struts can be screwed in, so that a kind of clip or snap-in connection between the transverse elements and the longitudinal structure is also produced here.

According to a preferred embodiment of the cell traverse according to the invention, the first longitudinal structure and/or the second longitudinal structure is designed as an essentially flat side wall. With an essentially flat side wall, a stable and process-reliable connection of the insert elements can be achieved, especially with a screw connection. The flat side wall, for example, can be made of sheet metal. To reduce weight and heat capacity, recesses are preferably provided in the side wall.

According to a preferred embodiment of the cell traverse according to the invention, the first longitudinal structure and/or the second longitudinal structure each comprise at least one, preferably at least two longitudinal struts. In the case of a plug-in connection, the transverse elements and sleeves can be advantageously pushed onto the longitudinal struts. In addition, a strut-like longitudinal structure provides an advantageous geometry for connecting insert elements to them by means of a clip connection. The longitudinal struts, for example, are tubular. In the case of several longitudinal struts, the longitudinal struts of a longitudinal structure are preferably arranged one above the other in the direction of insertion.

According to a preferred embodiment of the cell traverse according to the invention, at least some of the transverse elements are essentially tubular. In comparison to flat transverse elements, tubular transverse elements allow an effective cleaning of the cell traverse due to the lower blocking of cleaning fluid. Tubular transverse elements are particularly advantageous in combination with insert elements, which are connected to the frame structure by means of a clip connection, as the insert elements grip around the tubular transverse elements and can thus snap into place. Preferably, all transverse elements are essentially tubular. Preferably, the tubular transverse elements have an essentially round cross-section, at least in sections. However, it is also conceivable that an elliptical or angular cross-section of the tubular transverse elements is provided. In particular, the tubular transverse elements may have modifications which can be used, for example, to create a defined contact area with the packages or to attach insert elements, as described in more detail below.

According to a preferred embodiment of the cell traverse according to the invention, at least some of the transverse elements are essentially flat. By using flat transverse elements, high stability can be achieved, especially in the case of non-flat longitudinal structures of the frame structure (for example in the case of strut-like longitudinal structures, as is advantageous in the case of threading the transverse elements). Preferably, all transverse elements are essentially flat.

In accordance with a preferred embodiment of the cell traverse according to the invention, the frame structure of the cell traverse, in particular the longitudinal structures and/or the transverse elements, has contact elements projecting into the cells, at least in the region of the cells, for contacting packages to be filled or filled which are to be accommodated or taken up in the cells. Even if no insert elements are provided in the area of a cell, contact between the package and the frame structure can be prevented by the remaining frame structure in the area of the respective cell, thus reducing the contact area between frame structure and package. The contact elements are formed in particular by the longitudinal structures and/or transverse elements themselves. In the case of a flat longitudinal structure in particular, dentlike elevations in the direction of the cell interior may be provided in the flat longitudinal structure. Particularly in the case of (tubular) transverse elements, one or more circumferential thickenings may be provided on the transverse elements. Particularly in the case of flat transverse elements, a flat, elongated (particularly in the insertion direction) moulding in the direction of the cell interior may be provided on the transverse element.

Further advantageous exemplary embodiments of the invention can be found in the following detailed description of exemplary embodiments of the present invention, in particular in connection with the figures.

BRIEF DESCRIPTION OF THE DRAWING

Shown in the drawing:

FIGS. 4a-c show schematic views of further exemplary embodiments of insert elements.

DETAILED DESCRIPTION

Figure 1A:
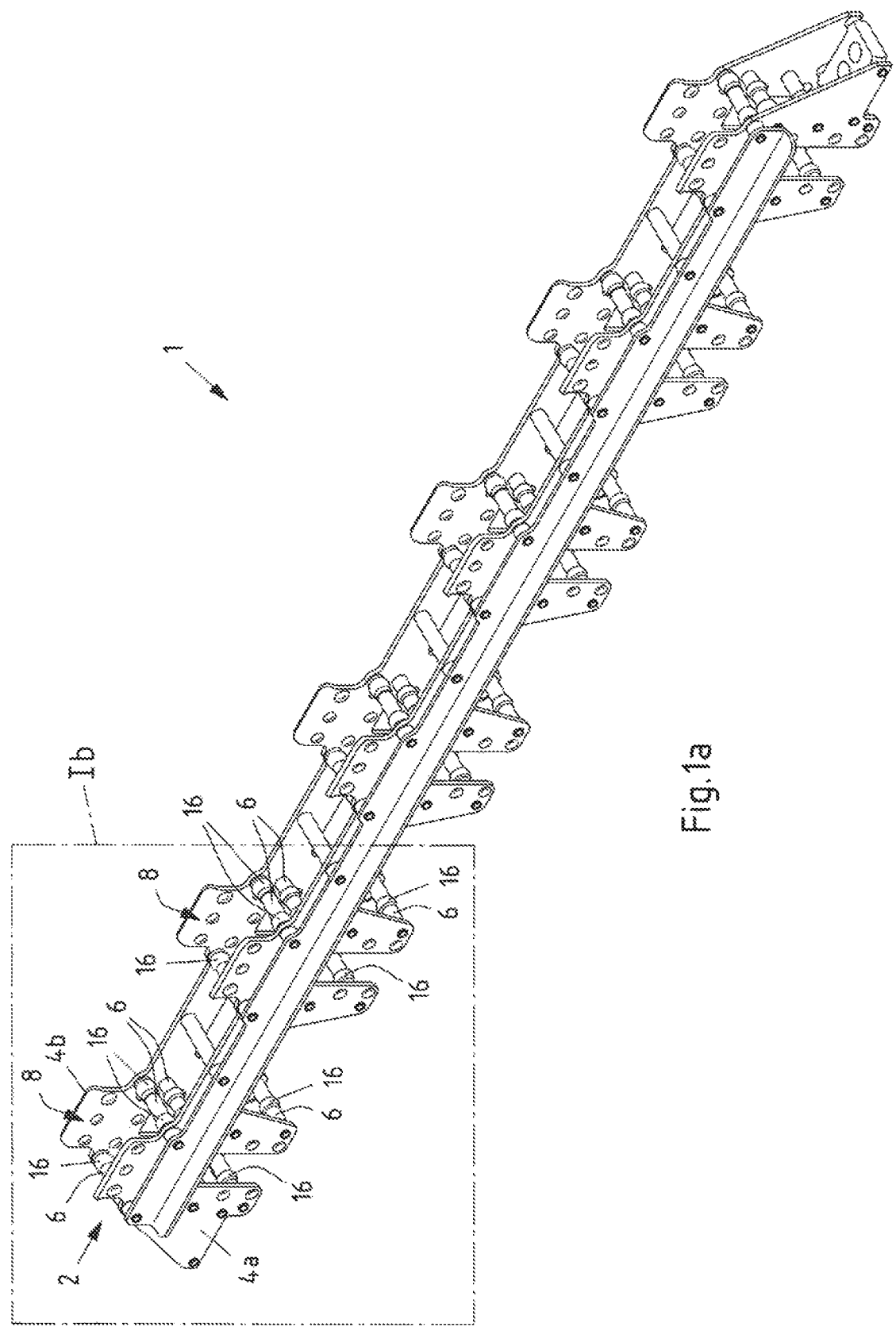
FIGS. 1a, b show perspective views of a first exemplary embodiment of a cell traverse, which can form a cell traverse according to the invention with insert elements.
Figure 1B:
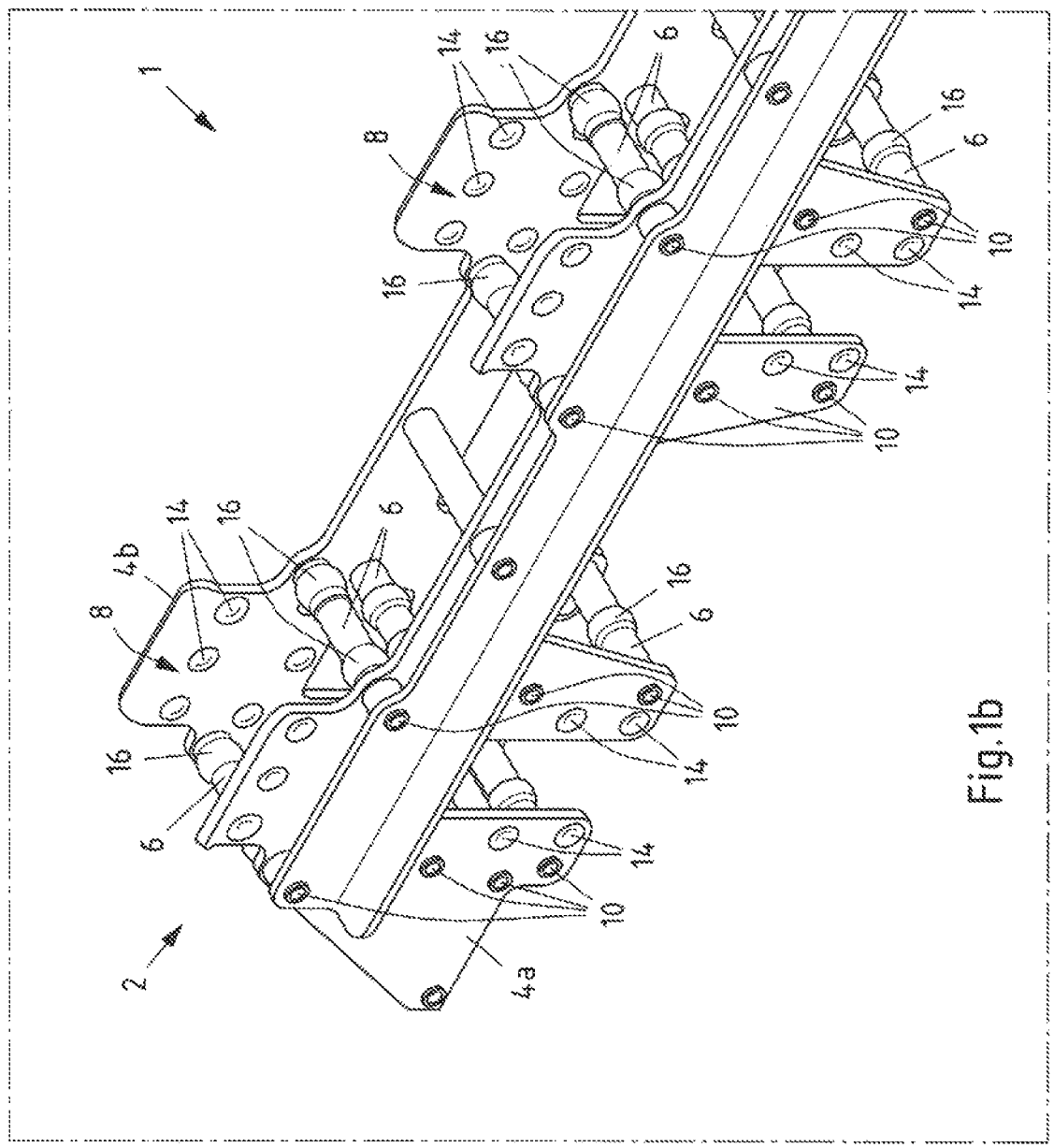
Figure 5:
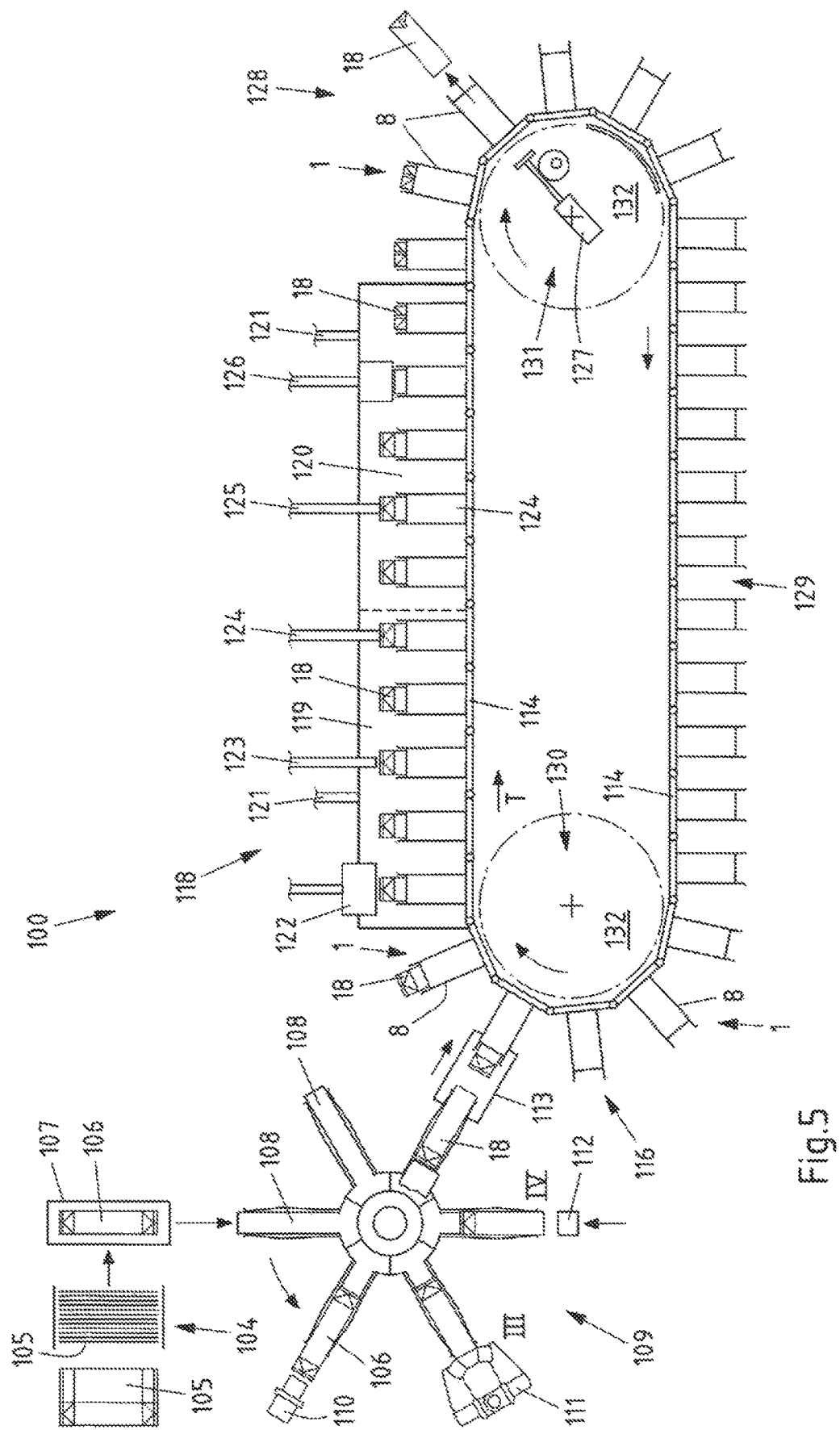
FIG. 5 shows an exemplary embodiment of a filling machine according to invention.

FIG. 1a-d show perspective representations of a first example of a cell traverse 1, from an oblique top with an enlarged section in FIG. 1b, which can form a cell traverse according to the invention with insert elements (see FIG. 2b, FIGS. 4a-c). The cell traverse 1 is suitable for an aseptic area of a filling machine (as illustrated in FIG. 5) for filling packages with flowable products. The cell traverse 1 comprises a frame structure 2 with a first lateral longitudinal structure 4a and a second lateral longitudinal structure 4b opposite the first longitudinal structure 4a. Between the first and second longitudinal structures 4a, 4b, a plurality of transverse elements 6 connecting the longitudinal structures 4a, 4b are arranged. Between the longitudinal structures 4a, 4b and the transverse elements 6, several cells 8 lying next to one another in the longitudinal direction of the cell traverse 1, but spaced apart, are formed to receive packages filled or to be filled (see FIGS. 2a, b or FIG. 5). The transverse elements 6 are connected to the longitudinal structures 4a, 4b on both sides by means of riveted joint 10, i.e. exclusively form-fit (and optionally force-fit). A screw connection instead of the rivet connection 10 would also be possible for a part or all transverse elements 6.

The first longitudinal structure 4a and the second longitudinal structure 4b are essentially flat side walls with 12 recesses for weight reduction. The transverse elements 6 are essentially tubular.

Figure 2A:
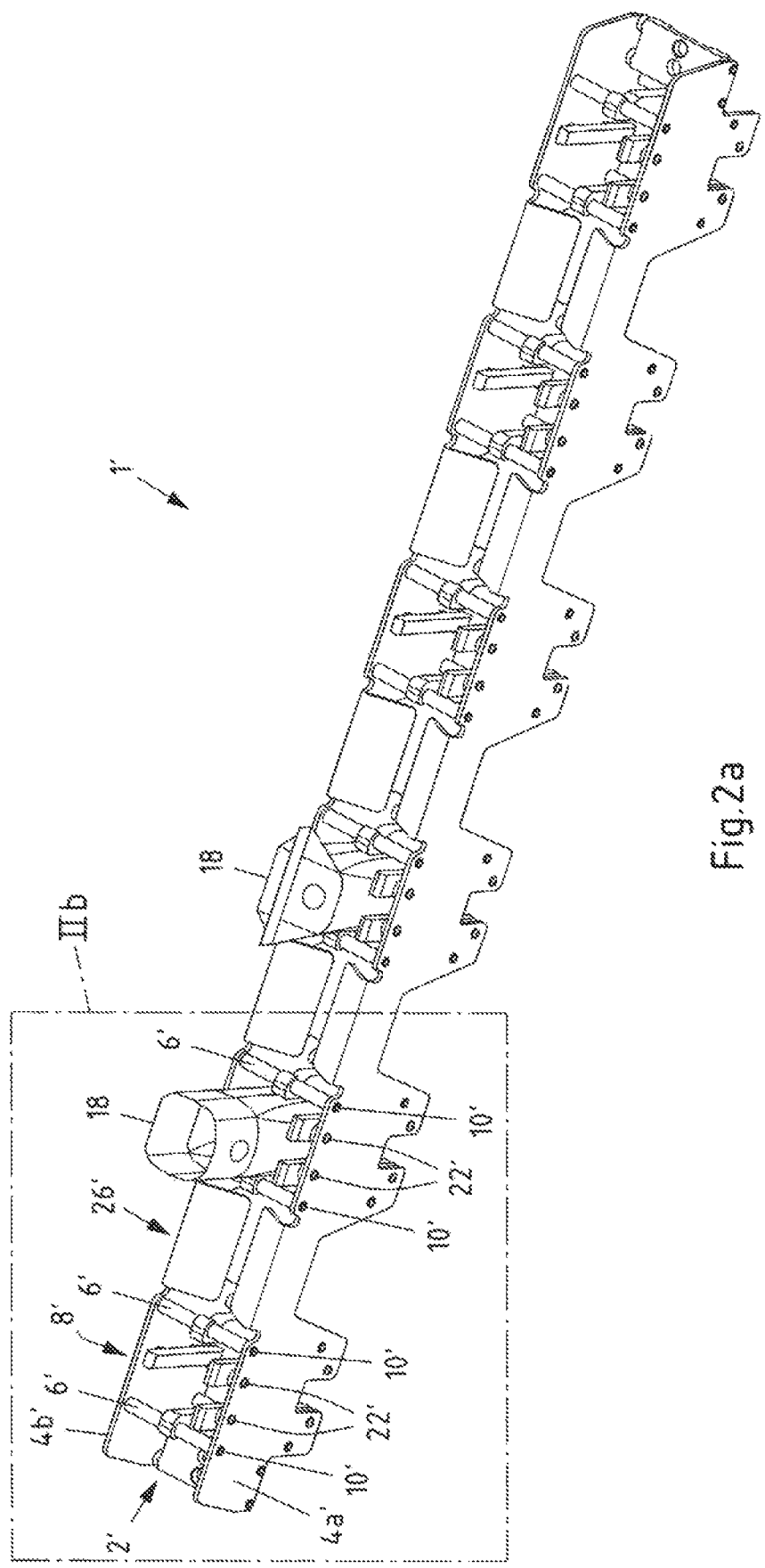
FIGS. 2a, b show perspective views of a second exemplary embodiment of a cell traverse according to the invention.

The longitudinal structures 4a, 4b and the transverse elements 6 of the frame structure 2 of the cell traverse 1 have contact elements 14, 16 projecting into the cells 8 in the area of the cells 8 for contacting packages 18 to be filled or filled (see FIGS. 2a, b or FIG. 5). The planar longitudinal structures 4a, 4b have dent projections 14 towards the cell interior, while the tubular transverse elements 6 each have one or two circumferential thickenings 16 to provide contact areas for the packages 18.

The cell traverse 1 can be described in more detail by means of insert elements, in particular in connection with FIGS. 2b and 4a-c, to represent an inventive cell traverse. In particular, the insert elements can provide the contact area for the packages and/or flow guiding structures, which can be arranged between two adjacent cells 8. These can, for example, be attached to the transverse elements 8 by means of a detachable connection, such as a clip connection.

Figure 2B:
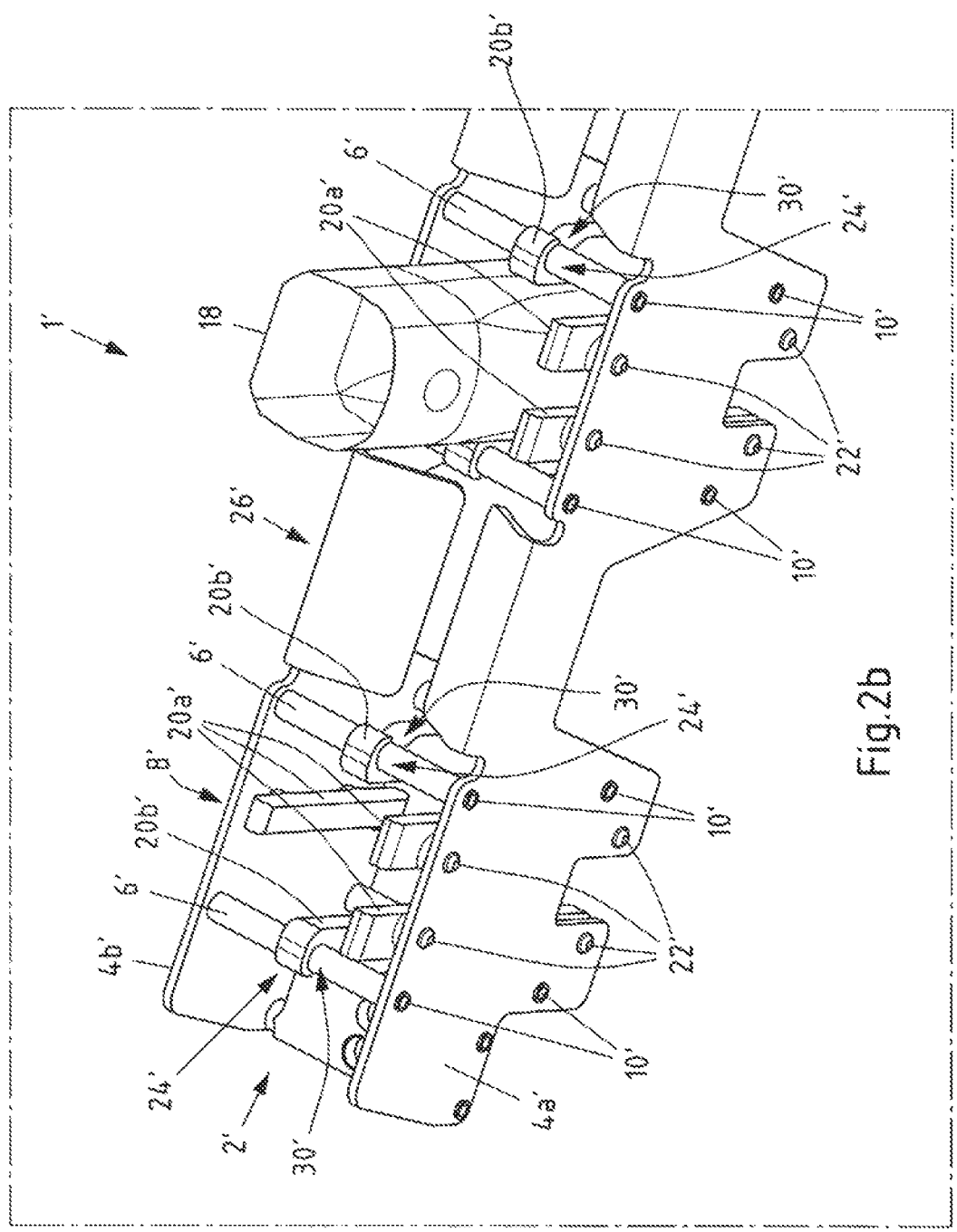

FIG. 2a, b show different perspective views of a second exemplary embodiment of a cell traverse 1' according to the invention from obliquely above with an enlarged section in FIG. 2b. Similar to the cell traverse 1, the cell traverse 1' also comprises a frame structure 2' with a first lateral planar longitudinal structure 4a' and a second lateral planar longitudinal structure 4b', between which a plurality of transverse elements 6' connecting the longitudinal structures 4a', 4b' are arranged, so that a plurality of adjacent but spaced apart cells 8' in the longitudinal direction of the cell traverse 1' are formed between the longitudinal structures 4a', 4b' and the transverse elements 6' for receiving packages 18 to be filled or filled. For illustrative purposes, packages 18 are shown here as open top packages and also as sealed packages inserted into cells 8' of cell traverse 1'. The transverse elements 6' in turn are essentially tubular. The transverse elements 6' are in turn connected on both sides to the longitudinal structures 4a', 4b' by means of a rivet joint 10'.

In contrast to the cell traverse 1 from FIG. 1, the longitudinal structures 4a', 4b' and the transverse elements 6' of the frame structure 2' themselves do not have integral contact elements.

Rather, the cell traverse 1' has insert elements 20a', 20b' in addition to the frame structure 2', which are detachably connected to the frame structure 2' in each case. The 20a' insert elements are each connected to a longitudinal structure 4a', 4b', while the 20b' insert elements are each connected to two transverse elements 6'. This provides a contact area of 30' for filled or to be filled packages which are to be received or taken up in the cells.

The detachable connection for the insert elements 20a' is achieved by means of a screw connection 22' at two points of the insert elements 20a' with the respective longitudinal structure 4a' or 4b', while the detachable connection for the insert elements 20b' is achieved by means of a clip connection 24' at two points of the insert elements 20b' with the respective transverse element 6'. The insert elements 20b' have snap-in grooves for this purpose, which the transverse elements 6' can partially enclose. In this case, the transverse elements 6' also have circumferential grooves in the connection area with the insert elements 20b' in which the snap-in grooves of the insert elements 20b' can engage. The insert elements 20a' and 20b' here are essentially elongated and made of a plastic, in particular a plastic based on polyethylene terephthalate. It is also possible that a metal reinforcement is provided within the insert elements 20a', 20b'.

Further alternative design examples of insert elements which can be connected to the frame structure (in particular the transverse elements) with a detachable clip connection are shown in FIGS. 4a-c.

Furthermore, the cell traverse 1' has several flow guiding structures 26', which are arranged between two adjacent cells 8' each. In this case, the flow guide structures 26' each comprise two guide plates which are formed as folded regions in one piece with the first and second lateral longitudinal structures 4a', 4b' respectively of the frame structure 2'.

However, it is also possible to design the flow guiding structures 26' as insert elements and, like the insert elements 20a', 20b', to detachably connect them to the frame structure 2'.

Figure 3B:
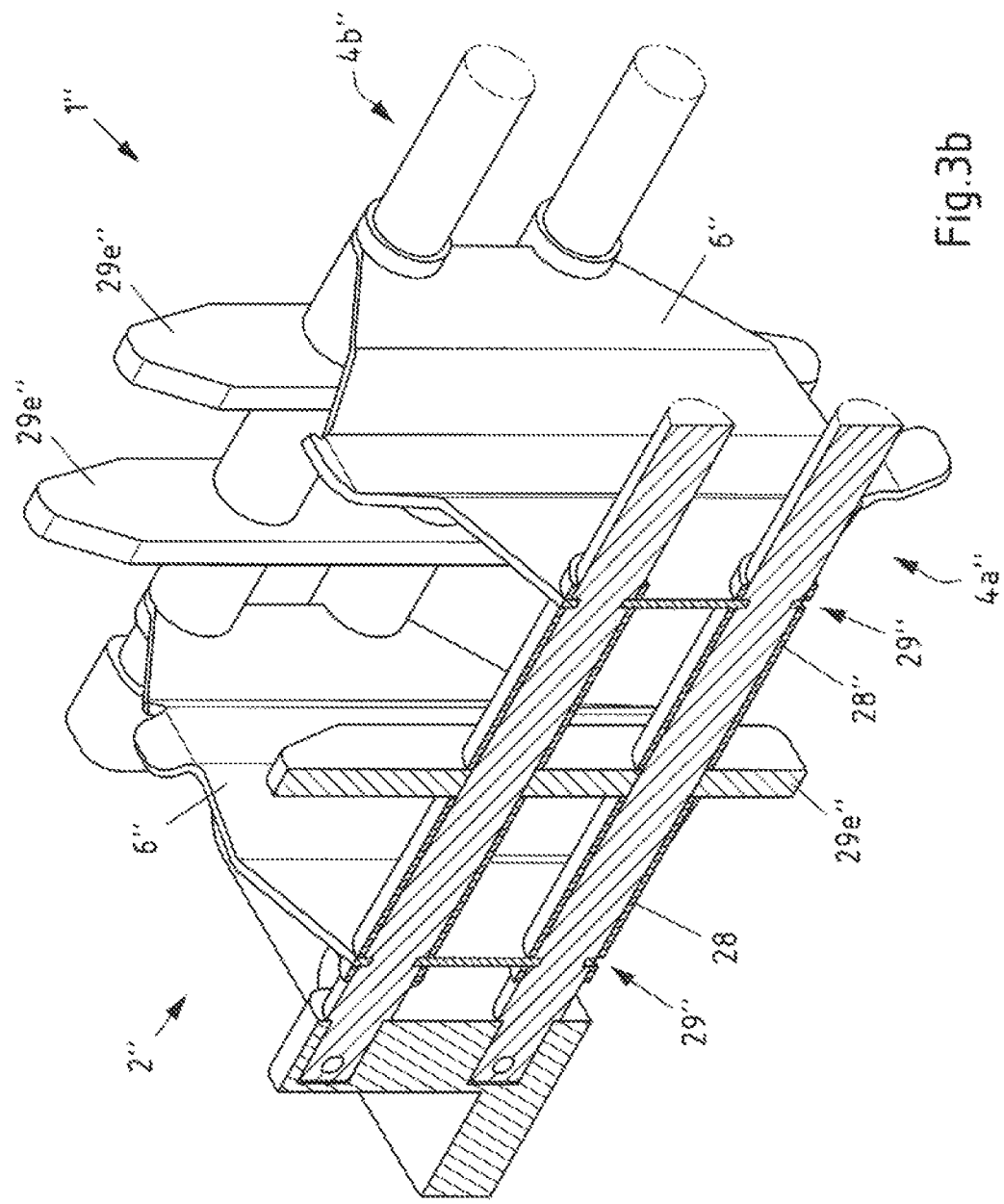
FIGS. 3a, b show perspective views of a third exemplary embodiment of an cell traverse according to the invention.

FIG. 3a, b show perspective views of a third exemplary embodiment of a cell traverse 1" according to the invention with an enlarged view of the partial cross section in FIG. 3b. Similar to the cell traverses 1, 1', the cell traverse 1" also comprises a frame structure 2" with a first lateral longitudinal structure 4a" and a second lateral longitudinal structure 4b", between which several transverse elements 6" connecting the longitudinal structures 4a", 4b" are arranged, so that between the longitudinal structures 4a", 4b" and the transverse elements 6" a plurality of spaced cells 8"' are formed lying adjacent one another in the longitudinal direction of the cell traverse 1" for receiving packages filled or to be filled.

In contrast to the cell traverses 1, 1', the first longitudinal structure 4a" and the second longitudinal structure 4b" of the cell traverse 1" comprises two longitudinal struts. Also deviating from the cell traverses 1, 1', the transverse elements 6" are essentially flat here. The transverse elements 6" here each have a flat, elongated mould running in feed direction, which defines the contact area with the inserted package. The transverse elements 6" are connected to the longitudinal structures 4a", 4b" by means of a plug-in connection. The plug-in connection is achieved here by engaging the transverse elements 6" in slots in the sleeves 28" which can be pushed onto the longitudinal struts of the longitudinal structure and by engaging in the grooves 29" of the longitudinal struts of the longitudinal structure 4a", 4b".

The guidance and contacting of packages 18 in the area of the longitudinal structure 4a", 4b" is provided by the insert elements 20e" and provides a contact area for filled or to be filled packages 18, which are accommodated or to be accommodated in the cells 8". The insert elements 20e" are realized by a plug-in connection with the longitudinal structure 4a", 4b", in which the insert elements 20e" are clamped (and thus locked) between two sleeves 28" in the longitudinal direction.

The cell traverse 1" can be supplemented by further insert elements, as described in particular in connection with FIGS. 2b and 4a-c. In particular, the insert elements can provide the contact area for the packages and/or flow guiding structures, which can be arranged between two adjacent cells 8. The insert elements can, for example, be attached to the longitudinal struts of the longitudinal structures 4a", 4b" by means of a detachable connection, such as a clip connection.

FIGS. 4b, c now shows two further examples of insert elements 20c' and 20d' in schematic sectional views, which can be used in particular like the insert elements 20b' shown in FIGS. 2b and 4a. The insert elements 20c' and 20d' each have two snap-in grooves 30' to be able to make a clip 24' connection with corresponding transverse elements 6'. Like the insert elements 20a', 20b', the insert elements 20c', 20d' provide a contact area 32' for filled or to be filled packages which are received or to be received in the cells.

To provide the contact area 32', the insert element 20d' has two resilient sections, each of which is locally thinned and has a one-sided free-swinging arm.

FIG. 5 now shows an example of a filling machine 100 in accordance with the invention for filling packages 18 with flowable products with an endlessly rotating transport device 114 for transporting the packages 18 through the filling machine 100. the transport device 114 comprises several exemplary cell traverses 1 in accordance with the invention which are arranged one behind the other in the transport direction T, but which can also be the cell traverses 1' or 1". The cell traverses 1 are mounted in such a way that the longitudinal direction of the cell traverses 1 is perpendicular to the transport direction T of the cell traverses 1. Due to the side view, only one of the cells 8 provided by the cell traverses 1 is visible in side view per cell traverse 1. In practice, a cell traverse today usually comprises four or six cells, and more rarely two or eight cells 8. However, cell traverses with a different number of cells 8 are also possible.

Filling machine 1 in this case also includes a forming device 103 for forming the packages to be filled 18. In principle, however, it is also possible to feed the filling machine 100 packages already open on one side for filling.

The filling machine 100 shown comprises a series of parallel processing lines by means of the several cells 8 of a cell traverse 1, of which only one processing line is shown in FIG. 5. Each processing line is assigned a bundle 104 of package blanks 105, the longitudinal edges of which are sealed together to form package sleeves 106 open on both sides. A transfer device 107 unfolds the package sleeves 106 and pushes them onto a mandrel 108 of a mandrel wheel 109.

The illustrated mandrel wheel 109 is turned cyclically, i.e. step by step. The 106 package sleeves are machined in different positions. First, an edge is heated with hot air using a heating unit 110 and then prefolded in a prefolder 111 in order to seal the prefolded edge to a base with a press 112. This results in a package 18 that is open on one side and tightly closed at one end, which is transferred from a feed device 113 to the endlessly circular transport device 114. The feeding can be done by simply stripping the package 18 from the mandrel 108 and inserting it into a cell 8 of a cell traverse 1. The packages 18 are inserted one after the other into separate, circularly guided cells 8 of the cell traverses 1 of the transport device 114, each of which is located in the feed area 116 of the transport device 114. The transport device 114 is thus an endlessly circulating cell chain or an endlessly circulating cell belt. In addition, it is conceivable that the cell traverses can be moved at least in sections by means of a linear motor.

The packages 18 are transported by the transport device 114 through an aseptic area 118, which is divided into a sterilisation zone 119 and a filling and sealing zone 120. Packages 18 do not have to be transported in a straight line, but can also be transported in at least one curve or even in a circle, depending on whether the filling machine 100 is a so-called inline or rotary machine. The aseptic area in the aseptic chamber 118 is flushed with sterile air via appropriate sterile air connections 121 to prevent the ingress of germs.

Sterile hot air is first blown into the open top packages 18 by a preheating device 122 in order to preheat the packages 18. A sterilizing agent is then blown into the packages in a sterilizing unit 123, which reacts more strongly in the preheated packages and condenses less. Hydrogen peroxide, for example, is used as a sterilizing agent. The hydrogen peroxide can be introduced together with steam and/or air into the one-sided open package 18. After sterilizing the packages 18, the inside of the packages 18 is dried in a drying device 124 by applying drying air. The drying air is preferably hot and sterile.

After the transition from sterilisation zone 119 to filling and sealing zone 120, the packages 18 open on one side are positioned under a filling device 125 and filled with food. The filled packages 18 are then closed with a closing device 126 by folding the upper open area of package 18 and sealing it. The sealed packages 18 are then discharged from the cells 8 of the transport device 114 in a discharge area 128 of the transport device 114 against the insertion direction via a discharge device 127 and then further processed as required. The now empty cells 8 of transport device 114 are moved over a return area 129 of transport device 114 further in the direction of mandrel wheel 109 in order to pick up further packages 18 there. In order to be able to transport the cells 8 endlessly back and forth, the feed area 116 and the discharge area 128 are assigned deflection areas 130, 131, in which so-called deflection rollers 132 are provided for the filling machine 100.

It is also conceivable that a cleaning device for the cell traverses is provided in particular in the return area 129 and/or a deflection area 130, 131.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A cell traverse for an aseptic region of a filling machine for filling packages with flowable products, the cell traverse comprising:
   a frame structure, comprising:
      at least one first lateral longitudinal structure,
      at least one second lateral longitudinal structure opposite the first lateral longitudinal structure, and
      a plurality of transverse elements arranged between the first and the second lateral longitudinal structures and connecting the first and the second lateral longitudinal structures, wherein between the first and second lateral longitudinal structures and the transverse elements a plurality of cells lying side by side in the longitudinal direction of the cell traverse are formed for receiving packages filled or to be filled, and
   insert elements which are each connected or connectable to the frame structure, at least some of the insert elements being detachably connected or connectable to the frame structure of the cell traverse,
   wherein
      the first lateral longitudinal structure and/or the second lateral longitudinal structure each comprises at least one, preferably at least two, tubular longitudinal struts and at least some of the insert elements are each connected or connectable to at least one, preferably at least two, tubular longitudinal struts of a lateral longitudinal structure of the frame structure,
   or
      at least some of the transverse elements are of tubular design and at least some of the insert elements are each connected or connectable to at least one, preferably two, transverse elements of the frame structure.

2. The cell traverse according to claim 1, wherein at least some of the insert elements provide a contact region for filled or to be filled packages which are received or to be received in the cells.

3. The cell traverse according to claim 1, wherein the insert elements have at least one resilient portion for providing the contact area.

4. The cell traverse according to claim 1, wherein at least some of the insert elements are flow guiding structures to direct gas flows within the aseptic area of the filling machine, which can each be arranged or are arranged between two adjacent cells.

5. The cell traverse according to claim 1, wherein at least some of the insert elements are connectable and/or detachable to the cell traverse without tools.

6. The cell traverse according to claim 1, wherein at least some of the insert elements are connected or connectable to the frame structure of the cell traverse by means of a clip connection, a screw connection and/or an in particular lockable plug-in connection.

7. The cell traverse according to claim 1, wherein at least part of the insert elements is made of a plastic, in particular a plastic based on polyethylene terephthalate (PET-P) or polyether ether ketone (PEEK), or comprises such a plastic.

8. The cell traverse according to claim 1, wherein at least a portion of the insert elements is made of a metal.

9. The cell traverse according to claim 1, wherein at least a portion of the insert elements has a metal reinforcement.

10. The cell traverse according to claim 1, wherein at least some of the transverse elements are connected exclusively form-fit and/or force-fit to the longitudinal structures.

11. The cell traverse according to claim 1, wherein the frame structure of the cell traverse, in particular the first and the second lateral longitudinal structures and/or the transverse elements, at least in the region of the cells has contact elements projecting into the cells for making contact with packages to be filled or filled which are to be received or received in the cells.

12. Use of a cell traverse according to claim 1 for a filling machine for filling packages with flowable products.

13. A filling machine for filling packages with flowable products comprising an endlessly circulating transport device for transporting the packages through the filling machine, wherein the transport device comprises a plurality of cell traverses according to claim 1.

14. A cell traverse for an aseptic region of a filling machine for filling packages with flowable products, the cell traverse comprising:
- a frame structure, comprising:
    - at least one first lateral longitudinal structure,
    - at least one second lateral longitudinal structure opposite the first lateral longitudinal structure, and
    - a plurality of transverse elements arranged between the first and the second lateral longitudinal structures and connecting the first and the second lateral longitudinal structures, wherein between the first and second lateral longitudinal structures and the transverse elements a plurality of cells lying side by side in the longitudinal direction of the cell traverse are formed for receiving packages filled or to be filled, and
- insert elements which are each connected or connectable to the frame structure, at least come of the insert elements being detachably connected or connectable to the frame structure of the cell traverse,
- wherein
    - the first lateral longitudinal structure and/or the second lateral longitudinal structure each comprises at least one, preferably at least two, tubular longitudinal struts and at least some of the insert elements are each connected or connectable to at least one, preferable at least two, tubular longitudinal struts of a lateral longitudinal structure of the frame structure,
    - or
    - at least some of the transverse elements are of tubular design and at least some of the insert elements are each connected or connectable to at least one, preferably two, transverse dements of the frame structure:
- wherein the roughness of the insert elements, in particular in the contact region provided, is at most 1.6, preferably at most 1.2.

15. A cell traverse for art aseptic region of a filing machine for filling packages with flowable products, the cell traverse comprising:
- a frame structure, comprising:
    - at least one first lateral longitudinal structure,
    - at least one second lateral longitudinal structure opposite the first lateral longitudinal structure, and
    - a plurality of transverse elements arranged between the first and the second lateral longitudinal structures and connecting the first and the second lateral longitudinal structures, wherein between the first and second lateral longitudinal structures and the transverse elements a plurality of cells lying side by side in the longitudinal direction of the cell traverse are formed for receiving packages filled or to be filled, and
- insert elements which are each connected or connectable to the frame structure, at least some of the insert elements being detachably connected or connectable to the frame structure of fire cell traverse,
- wherein
    - the first lateral longitudinal structure and/or the second lateral longitudinal structure each comprises at least one, preferably at least two, tubular longitudinal struts and at least some of the insert elements are each connected or connectable to at least one, preferably at least two, tubular longitudinal struts of a lateral longitudinal structure of the frame structure,
    - or
    - at least some of the transverse elements are of tubular design and at least some of the insert elements are each connected or connectable to at least one, preferably two, transverse elements of the frame structure,
- wherein the contact area provided by insert elements for filled or to be filled packages, which are received or to be received in the cells, is at most 35%, preferably at most 30%, particularly preferably at most 25% of the package outer surface area.

* * * * *

UNITED STATES PATENT AND TRADEMARK OFFICE
CERTIFICATE OF CORRECTION

Page 1 of 1

PATENT NO. : 11,001,402 B2
APPLICATION NO. : 16/732922
DATED : May 11, 2021
INVENTOR(S) : Bernd Lünnemann et al.

It is certified that error appears in the above-identified patent and that said Letters Patent is hereby corrected as shown below:

In the Claims

Column 15 Claim 14, Line 18, reads "to the frame structure, at least come of the insert" and should read --to the frame structure, at least some of the insert--

Column 16 Claim 15, Line 1, reads "A cell traverse for art aseptic region of a filing machine" and should read --A cell traverse for an aseptic region of a filling machine--

Column 16 Claim 15, Line 20, reads "the frame structure of fire cell traverse," and should read --the frame structure of the cell traverse,--

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*